United States Patent [19]

Nelson

[11] 4,102,900
[45] Jul. 25, 1978

[54] 3-(1'-SILYLOXY-3'-HYDROXYETHYL)-4-HYDROXY-6-SILYLOXYHEXANOIC ACID γ LACTONE DERIVATIVES

[75] Inventor: Norman A. Nelson, Galesburg, Mich.

[73] Assignee: The Upjohn Company, Kalamazoo, Mich.

[21] Appl. No.: 796,096

[22] Filed: May 12, 1977

Related U.S. Application Data

[62] Division of Ser. No. 676,893, Apr. 14, 1976, Pat. No. 4,048,194.

[51] Int. Cl.$^2$ ............................................. C07D 307/20
[52] U.S. Cl. ................................................... 260/343.6
[58] Field of Search ...................................... 260/343.6

[56] References Cited

U.S. PATENT DOCUMENTS 3,971,826  7/1976  Hess et al. ..................... 260/340.5 R Primary Examiner—Natalie Trousof
Assistant Examiner—Jane T. Fan
Attorney, Agent, or Firm—Robert A. Armitage

[57] ABSTRACT

The present specification provides novel intermediates and novel processes for the synthesis of Thromboxane $B_2$ (11a-homo-11a-oxa-PGF$_{2\alpha}$), its 15-epimer, and various carboxyl derivatives thereof. In particular, there are disclosed various bicyclic tetrahydrofuran-containing lactones useful in the above processes, and corresponding acyclic lactones.

2 Claims, No Drawings

3-(1'-SILYLOXY-3'-HYDROXYETHYL)-4-HYDROXY-6-SILYLOXYHEXANOIC ACID γ LACTONE DERIVATIVES

The present application is a divisional application of Ser. No. 676,893, filed Apr. 14, 1976, issued as U.S. Pat. No. 4,048,194 on Sept. 13, 1977.

The present invention relates to Thromboxane $B_2$ and associated intermediates and processes for which the essential material constituting disclosure therefor is incorporated by reference here from Ser. No. 676,890, filed Apr. 14, 1976, issued as U.S. Pat. 4,020,173 on Apr. 26, 1977.

I claim:

1. A thromboxane intermediate of the formula

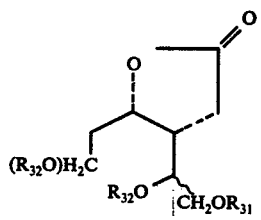

wherein $R_{31}$ is a hydroxy-hydrogen replacing group selected from the group consisting of $R_9$, $R_{10}$, and $R_{34}$;

wherein $R_{32}$ is $-Si(G_1)_3$, wherein $G_1$ is alkyl of one to four carbon atoms, inclusive, aralkyl of 7 to 12 carbon atoms, inclusive, phenyl, or phenyl substituted with one or two fluoro, chloro, or alkyl of one to four carbon atoms, inclusive, with the proviso that the various $G_1$'s are the same or different;

wherein $R_9$ is an acyl protecting group selected from the group consisting of (a) benzoyl;
(b) benzoyl substituted with one to 5 alkyl of one to 4 carbon atoms, inclusive, phenylalkyl of 7 to 12 carbon atoms, inclusive, or nitro, with the proviso that not more than 2 substituents are other than alkyl, and that the total number of carbon atoms in the substituents does not exceed 10 carbon atoms, with the further proviso that the substituents are the same or different;
(c) benzoyl substituted with alkoxycarbonyl of 2 to 5 carbon atoms, inclusive;
(d) naphthoyl;
(e) naphthoyl substituted with one to 9, inclusive, alkyl of one to 4 carbon atoms, inclusive, phenylalkyl of 7 to 10 carbon atoms, inclusive, or nitro, with the proviso that not more than 2 substituents on either of the fused aromatic rings are other than alkyl and the total number of carbon atoms in the substituents on either of the fused aromatic rings does not exceed 10 carbon atoms, with the further proviso that the various substituents are the same or different; and
(f) alkanoyl of 2 to 12 carbon atoms, inclusive;

wherein $R_{10}$ is a blocking group selected from the group consisting of (a) tetrahydropyranyl;
(b) tetrahydrofuranyl; and
a group of the formula

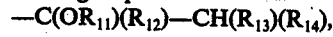

wherein $R_{11}$ is alkyl of one to 18 carbon atoms, inclusive, cycloalkyl of 3 to 10 carbon atoms, inclusive, aralkyl of 7 to 12 carbon atoms, inclusive, phenyl or phenyl substituted with one to 3 alkyl of one to 4 carbon atoms, inclusive, wherein $R_{12}$ and $R_{13}$ are alkyl of one to 4 carbon atoms, inclusive, phenyl, phenyl substituted with one, 2, or 3 alkyl of one to 4 carbon atoms, inclusive, or when $R_{12}$ and $R_{13}$ are taken together $-(CH_2)_a-$ or $-(CH_2)_b-O-(CH_2)_c$, wherein a is 3,4, or 5, and b is one, 2, or 3, and c is one, 2, or 3, with the proviso that b plus c is 2, 3, or 4, with the further proviso that $R_{12}$ and $R_{13}$ may be the same or different, and wherein $R_{14}$ is hydrogen or phenyl; wherein $R_{34}$ is an arylmethyl hydroxy-hydrogen replacing group selected from the group consisting of (a) benzyl,
(b) benzyl substituted by one to five alkyl of one to four carbon atoms, inclusive, chloro, bromo, iodo, fluoro, nitro, phenylalkyl of 7 to 12 carbon atoms, inclusive, with the further proviso that the various substituents are the same or different,
(c) benzhydryl,
(d) benzhydryl substituted by one to ten alkyl of one to four carbon atoms, inclusive, chloro, bromo, iodo, fluoro, nitro, phenylalkyl of 7 to 12 carbon atoms, inclusive,
(e) trityl, and
(f) trityl substituted by one to 15 alkyl of one to four carbon atoms, inclusive, chloro, bromo, iodo, fluoro, nitro, phenylalkyl of 7 to 12 carbon atoms, inclusive.

2. (3S, 4S)-3-[(1'S)-1'-trimethylsilyloxy-2'-benzoyloxyethyl]-4-hydroxy-6-trimethylsilyloxy-hexanoic acid γ-lactone, or its (1'R)-epimer, thromboxane intermediates according to claim 1.

* * * * *

UNITED STATES PATENT OFFICE
CERTIFICATE OF CORRECTION

Patent No. 4,102,900          Dated July 25, 1978

Inventor(s) Norman A. Nelson

It is certified that error appears in the above-identified patent and that said Letters Patent are hereby corrected as shown below:

The Title should read -- 3-(1'-SILYLOXY-2'-HYDROXYETHYL)-4-HYDROXY-6-SILYLOXYHEXANOIC ACID γ LACTONE DERIVATIVES -- instead of as shown on the patent.

*Signed and Sealed this*

*Twenty-seventh* Day of *February 1979*

[SEAL]

Attest:

RUTH C. MASON
*Attesting Officer*

DONALD W. BANNER
*Commissioner of Patents and Trademarks*